United States Patent
Buckman et al.

(10) Patent No.: US 8,357,831 B2
(45) Date of Patent: Jan. 22, 2013

(54) SURGICAL PACKING DEVICES

(76) Inventors: Robert F. Buckman, Elkton, MD (US); Jay A. Lenker, Laguna Beach, CA (US)

( * ) Notice: Subject to any disclaimer, the term of this patent is extended or adjusted under 35 U.S.C. 154(b) by 0 days.

(21) Appl. No.: 12/924,647

(22) Filed: Oct. 1, 2010

(65) Prior Publication Data
US 2011/0028934 A1    Feb. 3, 2011

Related U.S. Application Data

(63) Continuation-in-part of application No. 12/012,084, filed on Jan. 31, 2008, now Pat. No. 7,943,810, which is a continuation-in-part of application No. 11/087,224, filed on Mar. 23, 2005, now Pat. No. 7,329,792, which is a continuation-in-part of application No. 10/358,881, filed on Feb. 4, 2003, now Pat. No. 6,998,510.

(60) Provisional application No. 60/555,537, filed on Mar. 23, 2004, provisional application No. 61/277,927, filed on Oct. 1, 2009.

(51) Int. Cl.
*A61F 13/00* (2006.01)
*A61B 17/00* (2006.01)

(52) U.S. Cl. ............. 602/53; 602/60; 606/201; 606/203

(58) Field of Classification Search .................. 602/13, 602/47, 48, 58; 128/95.1, 96.1, 118; 606/201–204, 606/190–191
See application file for complete search history.

(56) References Cited

U.S. PATENT DOCUMENTS

| | | | |
|---|---|---|---|
| 390,354 A * | 10/1888 | Epple | 128/95.1 |
| 2,270,291 A * | 1/1942 | Grey | 128/108.1 |
| 3,874,387 A | 4/1975 | Barbieri | |
| 4,538,603 A | 9/1985 | Pawelchak et al. | |
| 4,787,379 A * | 11/1988 | Yeh | 128/95.1 |
| 5,181,914 A | 1/1993 | Zook | |
| 2,344,021 A | 3/1994 | Bouzianne | |
| 5,330,452 A | 7/1994 | Zook | |
| 5,376,067 A | 12/1994 | Daneshvar | |
| 5,423,736 A | 6/1995 | Cartwell et al. | |
| 5,447,505 A | 9/1995 | Valentine et al. | |
| 5,466,231 A | 11/1995 | Cercone et al. | |
| 5,470,625 A | 11/1995 | Perrault | |
| 5,478,308 A | 12/1995 | Cartwell et al. | |
| 5,538,500 A | 7/1996 | Peterson | |
| 5,662,679 A * | 9/1997 | Voss et al. | 606/204 |
| 5,800,372 A | 9/1998 | Bell et al. | |
| 5,843,060 A | 12/1998 | Cercone | |
| 6,096,943 A | 8/2000 | Maiwald | |
| 6,164,279 A | 12/2000 | Tweedle | |
| 6,343,604 B1 | 2/2002 | Beall | |
| 6,663,653 B2 * | 12/2003 | Akerfeldt | 606/203 |
| 7,309,498 B2 * | 12/2007 | Belenkaya et al. | 424/443 |
| 7,322,995 B2 * | 1/2008 | Buckman et al. | 606/157 |
| 2002/0029010 A1 | 3/2002 | Augustine et al. | |

FOREIGN PATENT DOCUMENTS
WO    00/25726 A2    5/2000

* cited by examiner

*Primary Examiner* — Kim M Lewis

(57) ABSTRACT

Devices and methods are disclosed for achieving hemostasis in patients who have received skin-penetrating wounds to the body in regions such as the shoulder, pelvis, neck, or groin, where standard bandages are difficult to apply and where large blood vessels exist which can hemorrhage severely. Such haemostatic packing devices and methods are especially useful in the emergency, trauma surgery, or military setting. The devices utilize packing pillows that are held in place by rigid structures that can cause the packing pillows to be brought into the wounds and be held in place while the packing pillows are inflated to fill the wounds, prevent bleeding, and tamponade hemorrhaging large blood vessels exposed therein.

16 Claims, 6 Drawing Sheets

SURGICAL PACKING DEVICES

RELATED APPLICATIONS

The present application is a Continuation-in-Part of U.S. patent application Ser. No. 12/012,084, file Jan. 31, 2008 now U.S. Pat. No. 7,943,810 which is a Continuation-in-Part of U.S. patent application Ser. No. 11/087,224, filed Mar. 23, 2005 now U.S. Pat. No. 7,329,782 which is a Continuation-in-Part of U.S. patent application Ser. No. 10/358,881 filed Feb. 4, 2003, now U.S. Pat. No. 6,998,510 the entirety of all of which are hereby incorporated herein by reference, and claims priority benefit under 35 USC §119(e) from U.S. Provisional Applications No. 60/555,537 filed Mar. 23, 2004, entitled "METHOD AND APPARATUS FOR PERIPHERAL HEMOSTASIS", and 61/277,927 filed Oct. 1, 2009, entitled METHOD AND APPARATUS FOR HEMOSTASIS, the entirety of both of which are hereby incorporated herein by reference.

FIELD OF THE INVENTION

The field of this invention is wound care during trauma surgery, general surgery, combat medicine, and emergency medical services. The invention is applicable to animals, especially including mammals, and is directed primarily at use on humans.

BACKGROUND OF THE INVENTION

As recently as the early 1990's, surgical operations for trauma were directed at the anatomic repair of all injuries at time of the initial operation. It was observed during these exercises that many patients became hypothermic, acidotic, and coagulopathic. Patients showing these three signs often died. Death often occurred in the operating room due to exsanguinations, or postoperatively, due to the complications of prolonged shock and massive transfusion to replace blood lost as a result of the trauma.

One of the most notable developments in the recent evolution of surgery has been the introduction of the concept of staged laparotomy to overcome the deficiencies of the repair all-at-once approach. This new strategy of staged laparotomy, employing new tactics that have been termed damage control, is now used in 10% to 20% of all trauma laparotomies.

This damage control strategy opens the way for a variety of new devices and methods for a) control of hemorrhage from solid organs or viscera, b) control of hemorrhage from peripheral wounds and peripheral vascular lacerations, and c) control of contents spillage from hollow viscera. Although there are procedures for controlling these injuries, none of these procedures utilize optimal devices or tactics in their execution. Each area offers technological opportunities to improve the devices and procedures for applying those devices.

There are situations, especially in the battlefield, where soldiers are placed at risk for penetrating injuries from bombs and projectiles. Soldiers are often equipped with body armor. However, this body armor generally protects the torso but not the arms, legs, and neck in the region where body flexibility is required. Thus, soldiers often incur injuries to the region just adjacent to the body armor, wherein such injuries are difficult to treat, hemorrhage significantly, and represent a real risk of loss of life, exsanguination cardiac arrest, or cerebrovascular dysfunction.

There are no devices, available today, which can be used to reliably treat injuries to individuals in the groin, shoulder, neck or other region immediately adjacent to the torso. New devices, procedures and methods are needed to support the strategy of damage control in patients who have experienced massive bodily injury in these regions. Such devices and procedures are particularly important in the emergency, military, and trauma care setting.

SUMMARY OF THE INVENTIONS

These inventions relate to improved haemostatic packing devices for use in trauma care. The present inventions include an impermeable barrier pack or wrap for a body appendage in a region located close to the torso. In these regions, it is not possible to wrap a bandage completely around the patient and to provide pressure to prevent loss of blood from a wound.

In some embodiments, the inventions include a C-shaped, or U-shaped, cuirass or other rigid or semi-rigid structural element that partially surrounds a hip, groin, shoulder, upper arm, upper leg, or neck. One side of the cuirass, near the opening and on the inside of the C, comprises a compression pack that can optionally be made to expand in volume, inward projection, pressure, or the like. The compression pack can be an inflatable bladder, a porous bladder filled with expandable hydrogel, a foam pillow, or the like. On the other side of the cuirass, near the opening and on the inside of the C, an expandable structural element is provided, which is adjustable and can project inward to varying degrees for the purpose of pulling the compression pack into a wound. The expandable structural element can include inflatable pillows or bladders, a jack-screw such as is used in a C-clamp, a scissor jack, a pneumatic or hydraulic piston, or the like. The C-shaped cuirass can be complete or it can be fabricated from segments, which can be stored and transported in a semi-flat configuration and then interconnected to form the C-shape, a structure that has increased volume and does not necessarily make it easy for transportation. An inflation system is also provided to inflate the compression pack, the expandable structural element, or both. Such inflation system can be a mouth operated inflation port with a valve or other closure. The inflation system can also include a piston that is advanced with a lever or, threaded rod and handle, jack-screw, or the like. Inflation can use fluids such as air, nitrogen, carbon dioxide, water, antimicrobial liquids, and the like.

The C-shaped cuirass and its components can be fabricated in different sizes, or it can be adjustable in size, or it can be a one-size-fits-all configuration. The C-shaped cuirass can be fabricated from polymeric materials such as, but not limited to, polyethylene, polypropylene, polycarbonate, polyetheretherketone (PEEK), polysulfone, polyester, acrylonitrile butadiene styrene, or the like. The cuirass can also be fabricated from metals such as, but not limited to, aluminum, stainless steel, nitinol, titanium, or the like. The cuirass is preferably open at one side but the closed side can comprise between about 160 to about 270 degrees of a circle. The opening can comprise between about 200 to about 90 degrees of the circle. The cuirass can be approximately C-shaped but not necessarily symmetrical as various shapes may be advantageous for surrounding the shoulder or certain points of the groin that might include somewhat distorted C-shapes with elongated upper and lower wings or even an open rectangular shape, for example. The C-shaped cuirass is configured with enough strength so as not to open, substantially distort, or fail under pressure significant enough to stop hemorrhage at systemic blood pressures up to about 100 to 300 mm Hg.

The compression pack can be fabricated from elastomeric materials such as C-flex, silicone elastomer, Hytrel, Pebax, polyurethane, polyester, polyethylene, polypropylene, polyamide, or other thermoplastic. The compression pack can also comprise a fabric fabricated from similar materials in a woven or knitted structure. The fabric like structure can be placed on the outer surface of the compression pack to enhance clotting because of its high surface area. Alternatively, the exterior surface of the compression pack can be made advantageously smooth to still cause tamponade but prevent adhesions that might interfere with later surgical reconstruction of the wound. The surface of the compression pack can be coated prior to application to the wound with antimicrobial agents such as silver azide, betadine, iodine, or antibiotics and it can also be coated with thrombogenic materials, such as fibrin glue, configured to enhance stoppage of bleeding from the wound. The compression pack can be configured to expand and fill whatever space is required to completely close off the wound to prevent hemorrhage. In other embodiments, the compression pack can be configured to adjust for spacing differences in one-size-fits all cuirass devices. The expansion can be caused by fluid (e.g. air, water, radiopaque dye) pressure injected through an injection port to fill a bladder, it can be caused by swelling of a hydrophilic hydrogel, swelling of a foam, or the like. Expansion can also occur by resilient expansion of compressed foam or other polymeric structure following insertion into the body through a laparoscopic instrument, tube, cannula, or the like.

Other aspects of the inventions include the methods of use. The methods of use include folding the pack in a container providing the minimum volume for portability and storage, especially in the field. Other embodiments include providing the pack in an aseptic container, wherein the pack has been sterilized using ethylene oxide, gamma irradiation, electron beam irradiation, steam sterilization, and the like. In some embodiments, the methods include removing the pack from its aseptic container, such as a Tyvek, heat sealed pouch, and assembling the relatively rigid cuirass structure from a plurality of parts, wherein the final assembly comprises an approximately C- or U-shape. The device can also be provided fully assembled in other embodiments. The methods of use include cleaning and preparing the wound by removing dirt, clothing, or other debris or contamination and then applying the sterile pressure pad into the wound and then making sure the cuirass has surrounded a sufficient part of the body that the expandable region on the opposite side may be activated to hold the pressure pack in place. The pressure pack is then inflated to its operational pressure or allowed to generate whatever pressure it is pre-set to generate. The expandable structural element is next activated to pull the pack into the wound to apply tamponade forces within the wound sufficient to generate hemostasis while not causing a tourniquet effect. In other embodiments, the pressure pack can be pulled into the wound first to cause tamponade, followed by expandable element being expanded to secure the pressure pack in place so that it is not easily disturbed or dislodged. In other embodiments, the expandable element is first expanded to pull the unexpanded pressure pack into the wound. The pressure pack is next inflated to generate the necessary hemostasis and tamponade.

The patient can now be transported to a medical facility where repair of the injured wound can be accomplished knowing that blood loss from the wound will be substantially reduced or prevented by the device, which is firmly in place and is resistant to jarring or coming loose.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE INVENTION

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

Figure 1:
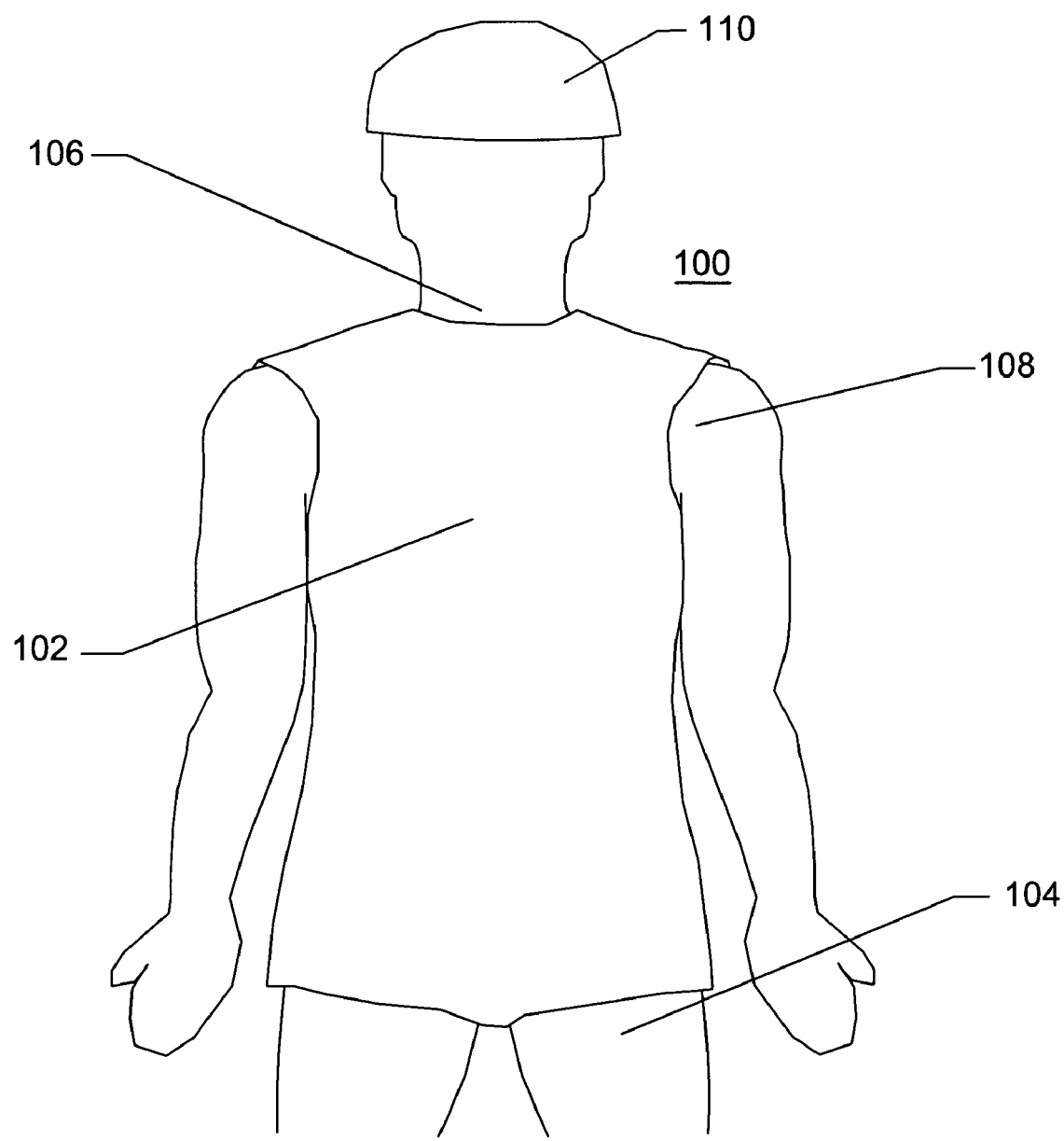
FIG. 1 illustrates the torso of a patient wearing body armor, according to aspects of the invention.

FIG. 1 illustrates a front view of a patient 100, looking posteriorly, wherein the patient 100 is wearing a protective vest 102 over their torso and a helmet 110 on their head. The patient 100 further comprises a shoulder 108, a groin 104, and a neck 106.

Referring to FIG. 1, the patient 100 is shown with protective gear similar to that used by military personnel. Other garments are not shown for simplicity. The protective vest 102 does not extend significantly over the groin area 104, the neck 106, or the shoulders 108 since mobility would be unduly restricted if such coverage existed.

Figure 2:
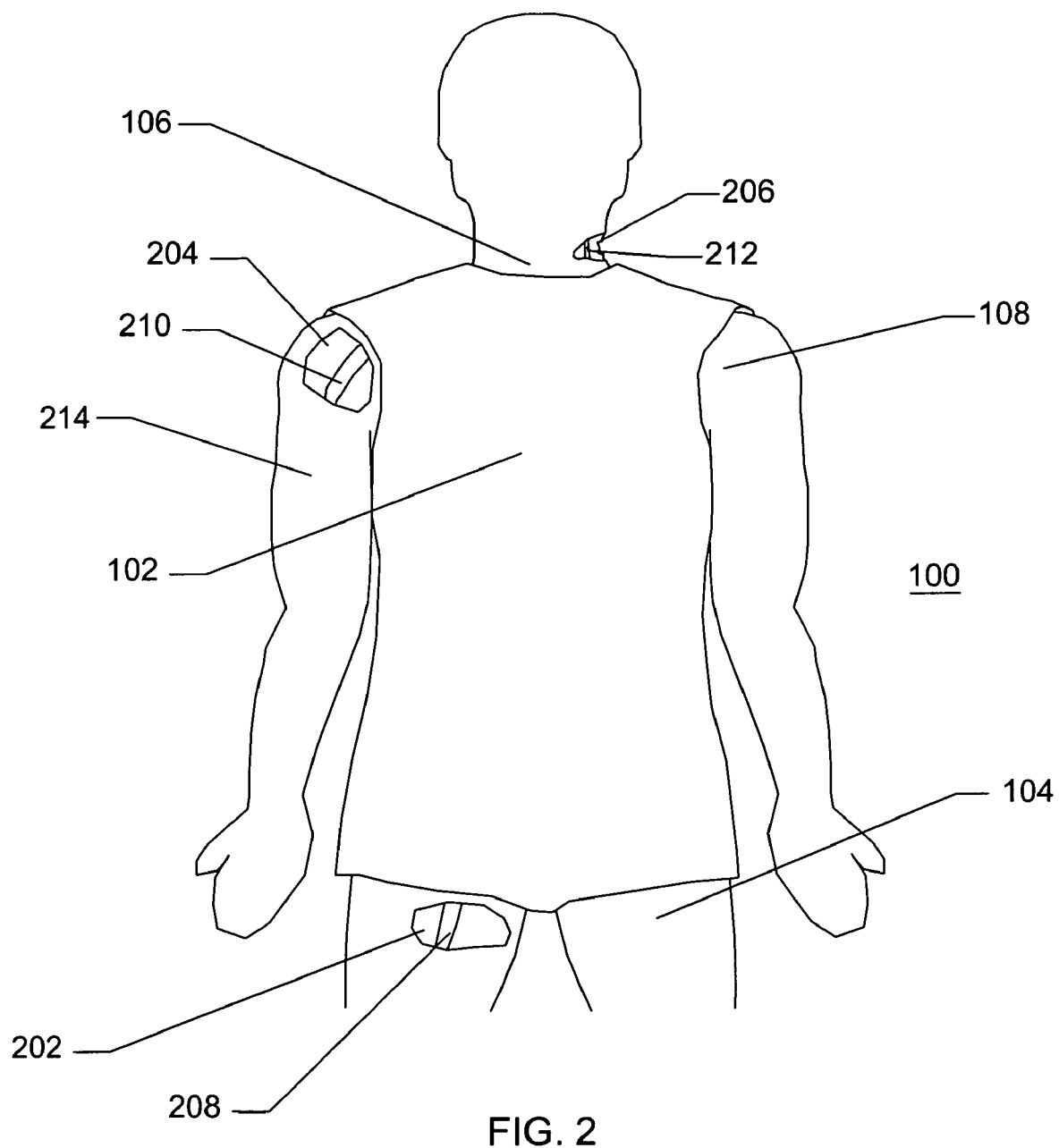
FIG. 2 illustrates wounds to a shoulder, a groin, and a neck just adjacent to the body armor, according to aspects of the invention.

FIG. 2 illustrates the patient 100 with their helmet 110 removed. The patient 100 has incurred a groin injury 202, a shoulder injury 204, and a neck injury 206, all of which are skin 214 penetrating. The groin injury 202 has exposed and endangers a femoral artery 208. The shoulder injury is an open wound and has endangered a large artery 210 running down the arm while the neck injury 206 has exposed and endangers a carotid artery 212.

Referring to FIG. 2, these types of injuries, if they result in damage to the blood vessels 208, 210, and 212 can be life threatening and can lead to exsanguination or sufficient loss of blood to cause severe long-term mental disability. The injuries 202, 204, and 206 are all located just adjacent to the body armor 102 in areas that are unprotected but are difficult to treat.

Figure 3:
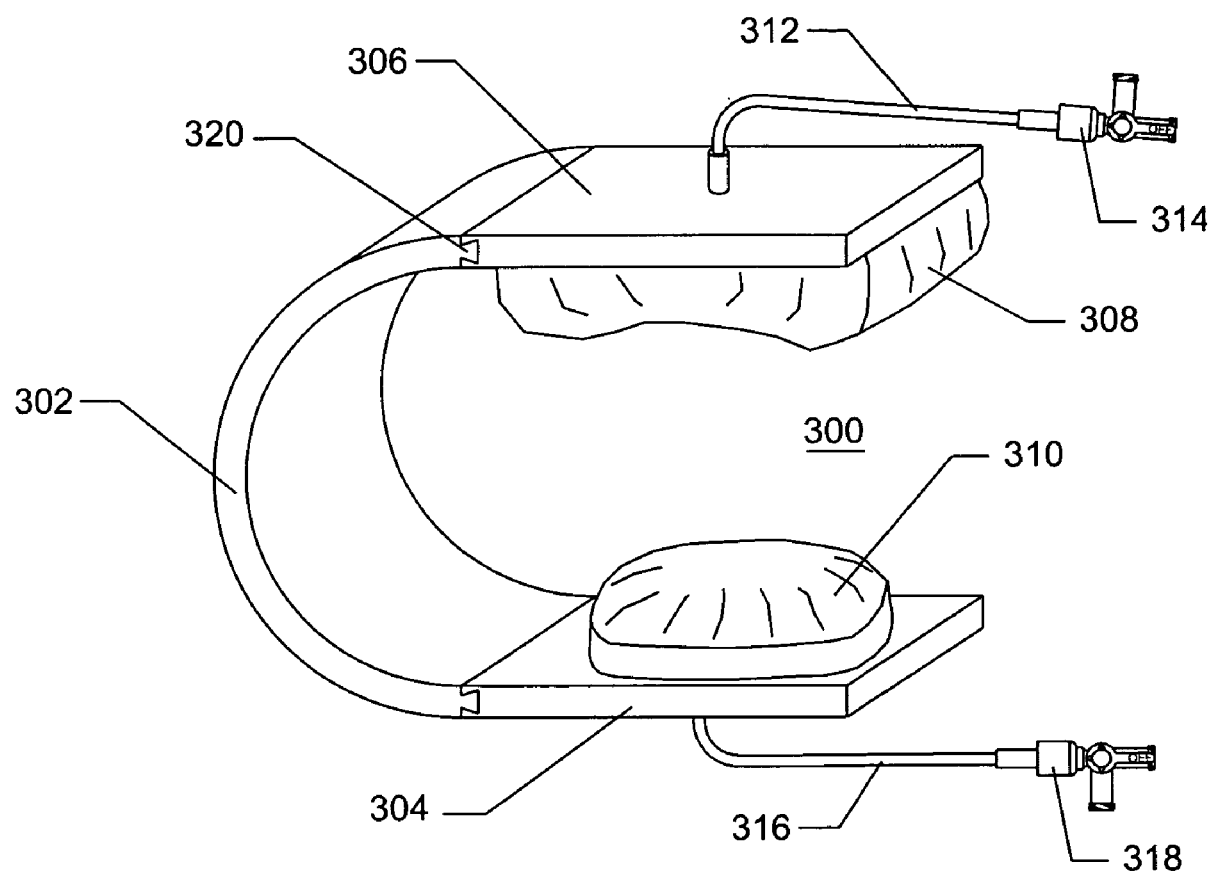
FIG. 3 illustrates a C-shaped wound treatment device with a wound pack and a compression mechanism, according to aspects of the invention.

FIG. 3 illustrates a severe wound pack system 300 comprising a three-part cuirass fabricated from a top plate 306, a bottom plate 304, and a curved connector plate 302. The plates 302, 304, and 306 are interconnected with a connector 320 that permits interlocking by sliding the plates together along their edges. The wound pack system 300 further comprises a compression pack 310, an expandable tightening pack 308, a tightening adjustment line or port 312, a tightening adjustment line valve 314, a compression adjustment line or port 316, and a compression adjustment valve 318.

Referring to FIG. 3, the compression pack 310 is affixed to the inside of the bottom plate 304 such that, upon expansion, the compression pack 310 projects inward and, optionally outward to a restricted degree. The expandable tightening pack 308 is affixed to the top plate 306 and is configured to be hollow and expand generally away from the top plate 306 to provide for gap adjustment between the two plates 304 and 306. The connector plate 302 is configured to permit substantially little or no opening of the distance between the top plate 306 and the bottom plate 304. The plates 302, 304, and 306 have the properties of rigidity and resistance to opening under pressure forces sufficient to hold the system 300 onto the patient and tamponade a wound with the compression pack 310. The valves 314 and 318 can be stopcocks or other types of inflation ports. The lumens of the valves 314 and 318 are operably connected to the lumen of the lines 312 and 316, respectively, which are, in turn, operably connected to the volume within the compression pack 310 and the expandable tightening pack 308. An optional strap can be affixed to, and used to secure, the open ends of the top plate 306 and the bottom plate 304 and the strap can be secured with a buckle, hook and loop fastener and the like. The connector plate 302 can be curved or straight, thus forming a rectangular structure with an open end. The connector plate 302 can comprise telescoping sections and can further comprise a threaded screw such as is found in a C-clamp to adjust the separation between the top plate 306 and the bottom plate 304. Manual rotation of a handle affixed to the threaded screw can cause the screw, which passes through either one of the top or bottom plates and is affixed to the other plate such that it can rotate but not move axially relative to that plate, to adjust the distance between the plates 304 and 306. The connector plate 302, the top plate 306, the bottom plate 304, or any combination thereof can be further reinforced with, for example I-beams, T-beams, or other structural support members either affixed externally or embedded therein to provide appropriate strength and resistance to distortion. The connector plate 302 can comprise a jack-screw and further comprise an alignment rod or element running along the same axis as the jack-screw to maintain the top plate 306 and the bottom plate 304 in correct alignment. The connector plate 302 can, in other embodiments, comprise a cam and lever system for opening and closing the jaws created by the top and bottom plates 306, 304, respectively.

Figure 4:
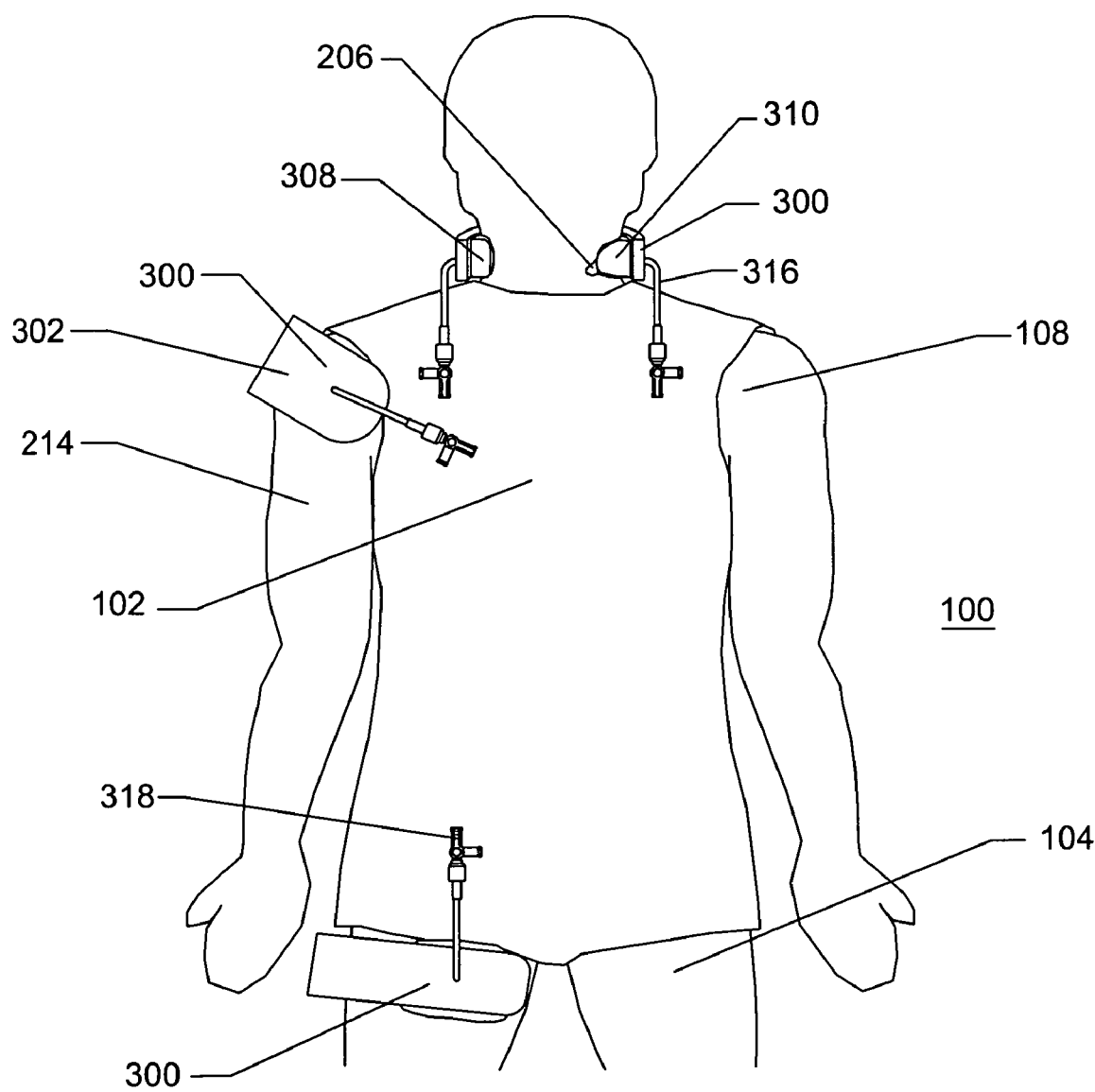
FIG. 4 illustrates the C-shaped wound treatment device applied to the groin wound, the neck wound, and the shoulder wound, according to aspects of the invention.

FIG. 4 illustrates the patient 100 with wound packs 300 applied to the groin injury 202, the shoulder injury 204, and the neck injury 206 (Refer to FIG. 2). The patient 100 is shown still wearing the body armor 102 so these devices can be used without removing certain protective gear. The compression pack 310 is illustrated inflated in the neck wound 206 while the expandable tightening pack 308 is also visible on the opposite side of the neck. The soft, pillow-like configuration of the expandable tightening pack 308, which can contain a saddle or concave region, provides for comfort and stability to main the tightening pack 308 in place. All packs 300 are shown with their inflation lines 316 and valves 318. The valves 318 are closed following inflation of the packs 300 to their desired degree of compression.

The compression pack 310 can be provided with a variety of outer surfaces to provide the correct amount of tamponade and thrombogenic properties to the tissues within it is being placed. Embodiments of the compression pack 310 are superior to other packing devices of the prior art in that they can apply pressure, in excess of 70 to 300 mm Hg, sufficient to staunch an arterial bleeding situation whereas the devices of the prior art are insufficiently resilient to push against tissue and stop the hemorrhage against systemic arterial pressure.

Figure 5:
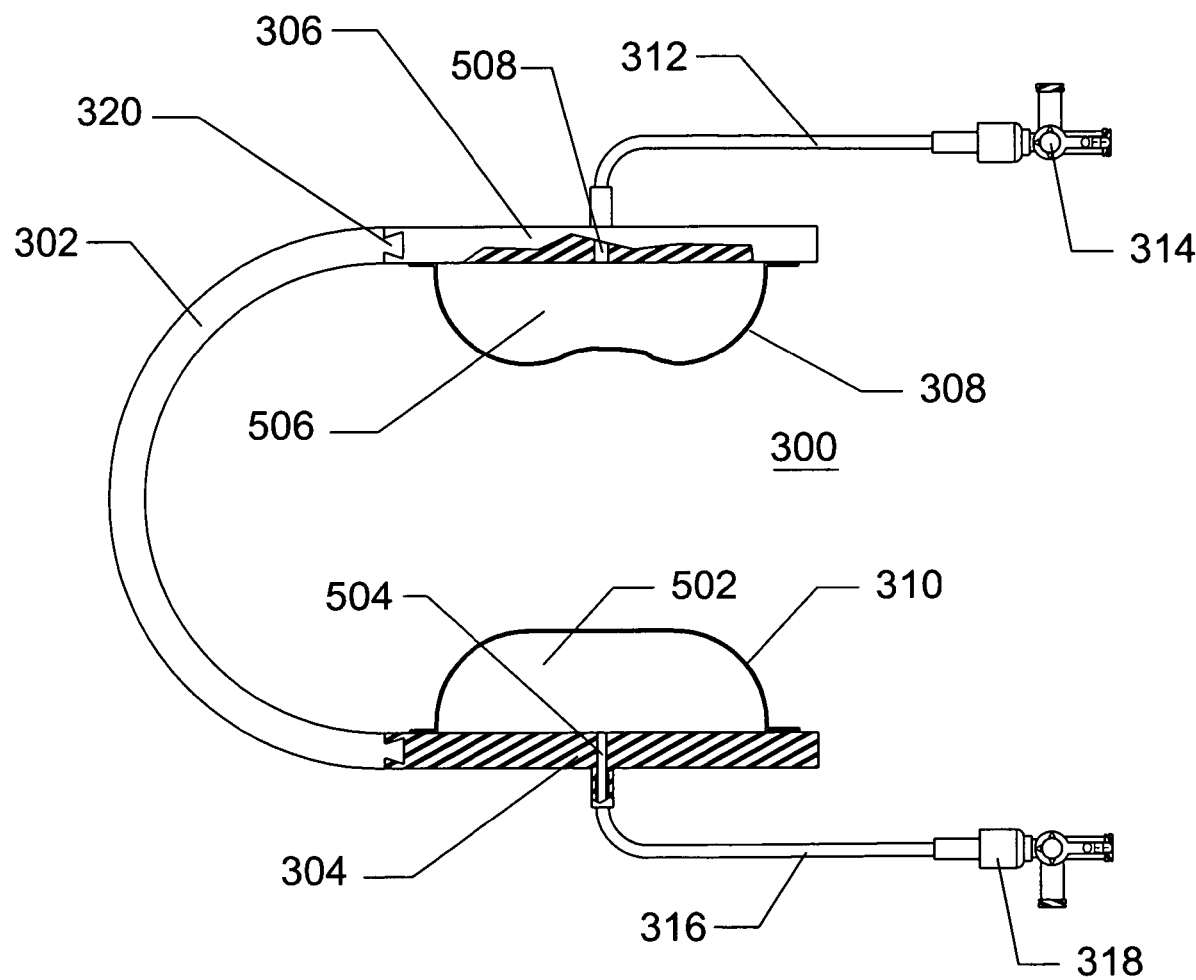
FIG. 5 illustrates a partial sectional view of the C-shaped wound treatment device, according to aspects of the invention.

FIG. 5 illustrates a side view of the wound pack 300 in partial breakaway, or cross-section. The lower plate 304 is shown in breakaway view as is the compression pack 310, further comprising the interior volume 502. The upper plate 306 is also shown in breakaway view with the tightening pillow 308 shown in sectional view with its interior volume 506 visible. In the illustrated embodiment, the tightening pillow 308 comprises a slight saddle shape on its inner edge, the edge that faces the patient. The tightening pillow 308 is inflated through the port 508 within the upper plate 306, which is operably connected to the lumen of the inflation line 312. The interior 502 of the compression pack 310 is operably connected to the inflation port 504, which is operably connected to the inflation line 316. The connectors 320 are visible and are shown as sliding dovetail attachments. The connectors 320 could be fabricated in other embodiments such as plates and screws, or the like. The pressures at which the interior of the compression pack 310 is inflated can approximate that of systemic arterial pressure, which can be vary from patient to patient and can range from 300 mm Hg to below 100 mm Hg in very sick patients.

The present invention is suitable for wounds to many parts of the body. The external hemostatic pack works on the arms, the legs, the head, a finger, the torso, or various extremities, etc., as well as the applications shown herein. The hemostatic packing device can be pressurized with fluids such as air, water, antibiotic material, saline, and the like. Such pressurization to levels at or above systemic arterial pressure assists in even distribution of said pressure and is capable of further assisting with hemostasis.

The inventions described herein and in U.S. patent application Ser. No. 12/012,084, the entirety of which is hereby incorporated herein by reference, describe packing devices to tamponade patient wounds, either open or closed. The devices and methods can be used to treat closed wounds of the abdomen by means of the laparoscopic, thoracoscopic, or general percutaneous delivery of a packing devices as described herein and inflation by means of a fluid pressure port, which can be on the pack or routed out the laparoscopic delivery system to the outside of the patient or by uptake of water or liquid from the patient, or by resilient expansion of the packing device internal structure. The resilient internal structure can be foam such as foam fabricated from polyurethane, polycarbonate urethane, or the like. The foam can be in multiple layers with different amounts of resiliency, pre-compression, or both. The laparoscopic instrument or introducer can be removed or left in place with the pack. Such packs introduced via cannula or instrumentation can be used to pack not only arm and leg wounds, but also abdominal, thoracic, groin, shoulder, or other injuries, for example. The pack can be permanently affixed at or near the distal end of the laparoscopic instrument, detachable, or separate. In some embodiments, the pack can be a bladder fabricated, at least in part, with fluid impermeable membrane chosen from materials such as, but not limited to, polyester, polyimide, polyamide, polyurethane, silicone, or the like.

The present invention includes apparatus and methods for treating wounds. The present invention, and the means described herein for accomplishing said wound treatment, may be embodied in other specific forms without departing from its spirit or essential characteristics. For example, although the preferred embodiment comprises a sterile bandage or packing device in an aseptic transfer package, a non-sterile device may also be appropriate in certain instances. Further, a strap means can be used to secure the U or C-shaped rigid cuirass to the patient in certain situations. The cuirass could be assembled to form a complete surround that does not compress the limb completely and thus does not generate a tourniquet effect. The shell could be square and the pillow be tightened with a plate and a jackscrew with a handle or knob. This shell, or cuirass, is able to force a fluid impermeable barrier or dams, pre-mounted to a rigid or semi-rigid backbone, frame, or scrim, against the patient to force the dams into the skin without causing the tourniquet effect of a tightly wrapped strap. Thrombogenic or antimicrobial agents could be applied to any region of the peripheral hemostasis system. Adjustment means, such as a jackscrew or a lever and ratchet is used to control the amount of force with which the dams are impressed into the skin to cause the fluid-tight seal. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

Figure 6:
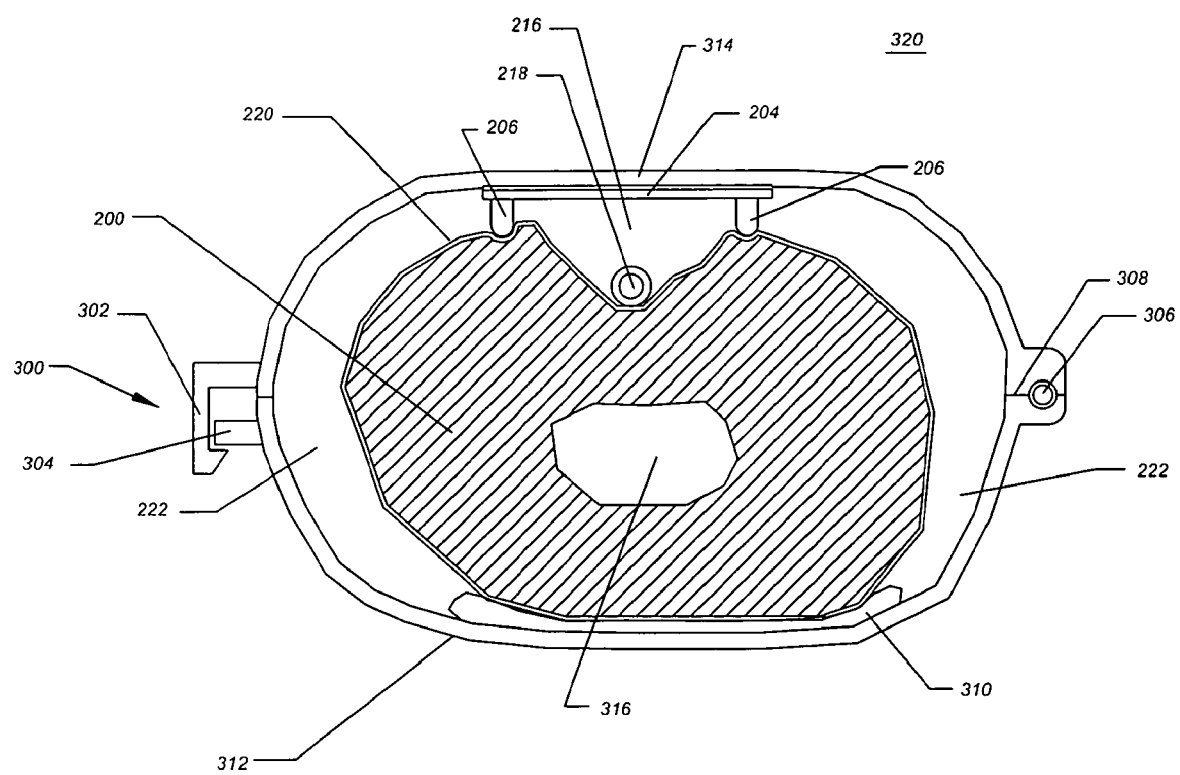
FIG. 6 illustrates a cross-sectional view of an appendage with a wound and a peripheral hemostasis system attached thereto. The peripheral hemostasis system includes a rigid or semi-rigid cuirass to apply a fluid-tight barrier over the wound without creating a tourniquet effect, according to aspects of the invention.

FIG. 6 illustrates another embodiment of the peripheral hemostasis system 320 further comprising an upper shell member 314, a lower shell member 312, a hinge 306, a separation line 308, a latch 300 further comprising a tab 302 and a catch 304, a dam 206, an optional pad 310, and a fluid impermeable barrier 204. The peripheral hemostasis system 320 is wrapped around a limb 200 further comprising a bone 316, a blood vessel 218, a wound 216, and a skin layer 220. A gap 222 exists in at least one circumferential region between the limb 200 and the shell halves 312 and 314.

Referring to FIG. 6, the upper shell member 314 and the lower shell member 312 are rigid or semi-rigid structures that are rotatably affixed to each other by the hinge 306. The upper shell member 314 abuts the lower shell member 312 at the separation line 308, which exists on the hinge 306 side and the latch 300 side, when the shell 320 is closed around limb 200. This type of device 320 is also known as a cuirass. The fluid impermeable barrier 204 and the dams 206 surrounding the barrier 204 are affixed to the inner aspect of the upper shell member 314. The pad 310 is affixed to the interior aspect of the lower shell member 312. The latch 300 is preferably formed integrally to the upper shell member 314 and the lower shell member 312 and is a simple snap latch. Other latches 300 include, but are not limited to, snaps, buckles, zippers, buttons, Velcro, pushbutton latches, slide latches, bayonet catches, screw fixation, and the like.

The upper shell member 314 and the lower shell member 312 are fabricated by injection molding, metal forming, die stamping, blow molding, laminating, or the like, using materials including, but not limited to, thermoplastics, steel, aluminum, polysulfone, polystyrene, polyethylene, polyester, polycarbonate, polyvinyl chloride, and the like. The latch 300 components 302 and 304 are similarly fabricated and are either integral to the upper and lower shell members 314 and 312 or they are separately fabricated and affixed using adhesives, screws, rivets, or the like. Provision for size adjustability can be made with the peripheral hemostasis system 320 using, for example, internal cinches and straps, different thickness padding 310, variable catch locations on the latch 300, a multi position hinge 306, and the like. The peripheral hemostasis system 320 creates a closure and sealing force directed substantially along only one axis. The peripheral hemostasis system 320 does not, in this embodiment, create uniform radially inwardly directed forces that completely circumnavigate the appendage, a situation that could reduce venous return blood flow and cause a tourniquet effect.

The peripheral hemostasis system 320 is provided opened and in a container which is sealed from contamination. The peripheral hemostasis system 320 is preferably sterilized using ethylene oxide, gamma radiation, electron beam irradiation, or the like prior to use. A single or double aseptic pouch, such as one fabricated from Tyvek, is a preferred container for the peripheral hemostasis system 320. The peripheral hemostasis system 320 is removed from its aseptic container and placed around the limb 200 so that the dams 206 impinge on the skin 220 surrounding the wound 216. The upper shell member 314 is brought into apposition with the lower shell member 312 and the latch 300 is engaged making sure a tight seal occurs between the dam 206 and the skin 220. Thus, blood escaping from the blood vessel 218 cannot escape the environs of the wound 218 and the patient cannot bleed to death. At the minimum, blood loss is greatly slowed minimizing the chance of bleeding to death during transport to a medical facility. The space 222 between the shell parts 314 and 312 and the limb 200 make sure that force is only applied in one direction to the limb. Force in the orthogonal direction is not applied so a complete seal is not created around the limb 200. Thus, the potential for venous return being compromised is reduced and the tourniquet effect is eliminated or reduced.

Applicant asserts that no new matter has been added.

What is claimed is:

1. An apparatus adapted to be applied to a human body to prevent hemorrhage from a skin-penetrating wound comprising:
   a substantially rigid or semi-rigid structure further comprising a top plate, a bottom plate, and a connector region, wherein the substantially rigid or semi-rigid structure forms a U, C, or open rectangular shape that is open on at least three sides;
   a wound compression pillow, affixed to an inside aspect of the bottom plate that can be expanded into the wound to provide compression and tamponade of the wound;
   a liquid impermeable membrane affixed between the wound compression pillow and the inside aspect of the bottom plate;
   at least one raised dam, affixed to the liquid impermeable membrane, wherein the dam completely surrounds the wound compression pillow and projects away from the liquid impermeable membrane such that the dam forms an edge seal to prevent the escape of blood from the wound;
   a mechanism to expand the wound compression pillow;
   a padded region affixed to an inside aspect of the top plate, wherein the padded region is configured to remain stable against the body and provide for force distribution to maximize comfort, and
   a mechanism to expand the padded region to adjust the tightness with which the apparatus holds the wound compression pillow in the wound, wherein the pressure distribution of the wound compression pillow can be adjusted to exceed systemic arterial pressure and thus provide for hemostasis of the wound.

2. The apparatus of claim 1 wherein said substantially rigid or semi-rigid structure does not touch the body around which it is applied at substantially all points along an interior surface of the substantially rigid or semi-rigid structure, so as to minimize any tourniquet effects.

3. The apparatus of claim 1 wherein the mechanism to expand the wound compression pillow further comprises a hollow, flexible, inflatable wound compression pillow, an inlet port, a valve to open and close access to the inlet port, an inflation device, and a volume of inflation fluid, wherein the inflation device delivers or removes the inflation fluid to the hollow wound compression pillow under a controlled pressure.

4. The apparatus of claim 1 wherein the mechanism to expand the padded region further comprises a hollow, flexible, padded region, an inlet port, a valve to open and close access to the inlet port, an inflation device, and a volume of inflation fluid, wherein the inflation device delivers the inflation fluid to the padded under a controlled pressure.

5. The apparatus of claim 1 wherein the top plate, the bottom plate, and the connector plate are provided as a pre-assembled or unitary structure.

6. The apparatus of claim 1 wherein the top plate, the bottom plate, and the connector plate are provided as a plurality of parts which are assembled prior to use.

7. The apparatus of claim 1 wherein the wound compression pillow can be affixed to the bottom plate by the user.

8. The apparatus of claim 1 wherein the distance between the top plate and the bottom plate can be adjusted.

9. A method of minimizing hemorrhage from a skin-penetrating wound in a patient near the torso comprising the steps of:
affixing a wound tamponade pack to a first side of a cuirass;
surrounding the wound tamponade pack with at least one raised dam that projects away from the first side of the cuirass such that the raised dam forms an edge seal to prevent the escape of blood from the wound;
affixing a support to a second side of a cuirass;
wrapping the cuirass around the body such that the wound tamponade pack is inserted into the wound;
adjusting the distance between the first side of the cuirass and the second side of the cuirass such that the wound tamponade pack is firmly held in place;
inflating the wound tamponade pack with fluid to generate sufficient pressure to tamponade hemorrhage within the wound; and
moving the patient to another location for repair of the wound.

10. The method of claim 9 further comprising the step of applying thrombogenic material to the exterior of the wound tamponade pack.

11. The method of claim 9 further comprising the step of applying a strap and fastener to close off an open side of the cuirass.

12. The method of claim 9 wherein the cuirass is a substantially rigid "C" or "U" shaped structure configured to be placed over the wound and surrounding body tissue.

13. The method of claim 9 further comprising the step of applying an antimicrobial agent to the exterior of the wound tamponade pack.

14. The method of claim 9 further comprising the step of providing at least the wound tamponade pack in sterile condition.

15. The method of claim 9 further comprising the step of adjusting the distance between the first plate and the second plate to achieve proper alignment of the wound tamponade pack within the wound.

16. The method of claim 9 further comprising the step of tightening a jackscrew or cam lever system or inflating a bladder to adjust the position of the wound tamponade pack.

* * * * *